(12) United States Patent
Goodwin et al.

(10) Patent No.: US 7,608,840 B2
(45) Date of Patent: Oct. 27, 2009

(54) SYSTEM AND METHOD EMPLOYING PHOTOKINETIC TECHNIQUES IN CELL BIOLOGY IMAGING APPLICATIONS

(75) Inventors: Paul C. Goodwin, Shoreline, WA (US); Carl S. Brown, Seattle, WA (US); Steven A. Reese, Shoreline, WA (US)

(73) Assignee: Applied Precision, LLC, Issaquah, WA (US)

( * ) Notice: Subject to any disclaimer, the term of this patent is extended or adjusted under 35 U.S.C. 154(b) by 0 days.

(21) Appl. No.: 12/185,775

(22) Filed: Aug. 4, 2008

(65) Prior Publication Data

US 2009/0026386 A1    Jan. 29, 2009

Related U.S. Application Data

(63) Continuation of application No. 10/872,329, filed on Jun. 18, 2004, now Pat. No. 7,408,176.

(60) Provisional application No. 60/480,432, filed on Jun. 19, 2003.

(51) Int. Cl.
*G01N 21/64* (2006.01)
(52) U.S. Cl. .................... 250/459.1; 250/458.1
(58) Field of Classification Search ............ 250/458.1, 250/459.1, 484.2
See application file for complete search history.

(56) References Cited

FOREIGN PATENT DOCUMENTS

| | | | |
|---|---|---|---|
| EP | 1 139 291 A | 10/2001 | |
| WO | 01/20044 A | 3/2001 | |
| WO | 03/014400 A | 2/2003 | |
| WO | 03/079664 A | 9/2003 | |
| WO | 2004/083832 A | 9/2004 | |

OTHER PUBLICATIONS

Sibarita, J-B et al.: Ultra-fast 4D microscopy and high throughput distributed deconvolution, 2002 IEEE International Sympo sium on Biomedical Imaging, Jul. 7, 2002, pp. 769-772.
Kato, N: Structural analyses of living pl ant nuclei, Genetic Engineering 25:65-90 (2003).
Tsien R Y: The green fluorescent protein, Ann . Rev. Biochem. 67:509-544 (1998).

*Primary Examiner*—David P Porta
*Assistant Examiner*—Mark R Gaworecki

(57) ABSTRACT

A system and method employing photokinetic techniques in cell biology imaging applications are disclosed. Systems and methods of acquiring image data of an object may comprise: selectively inducing photoactivation of material at a site on the object; performing an optical axis integration scan; simultaneously executing a time delay integration scan sequence; and processing acquired image data in accordance with one or more desired analyses. Various methodologies and applications may include, inter alia, selective photobleaching of a site on the object, diffusion rate, velocity, and wave-front propagation analyses, multi-dimensional analyses of dispersion characteristics, biomolecular binding in cellular organelles, and photoactivation assisted systematic image segmentation for the study of cellular components.

1 Claim, 10 Drawing Sheets

A. Isotropic Dispersion
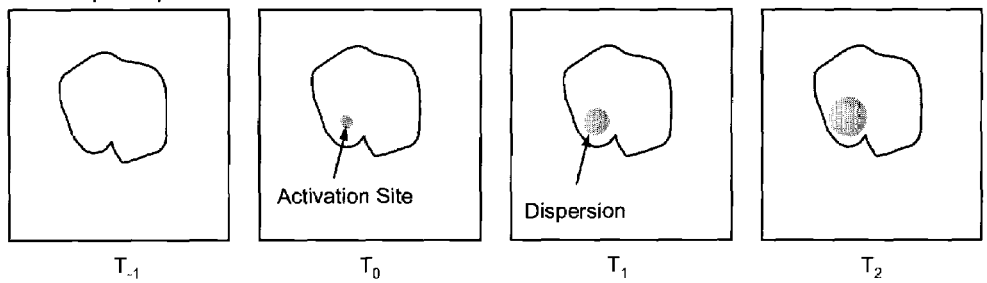
B. Anisotropic Dispersion
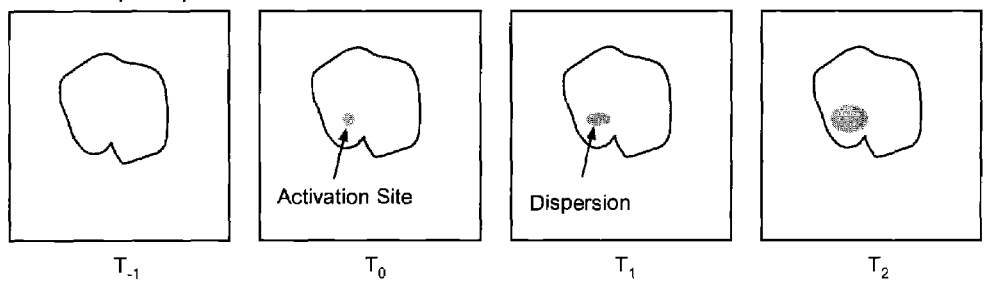
C. Iso-Velocity Plots
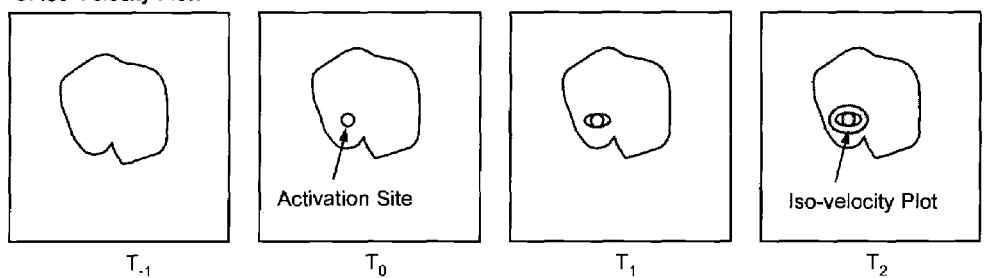
D. Dispersion Analysis to Reveal Cellular Structure
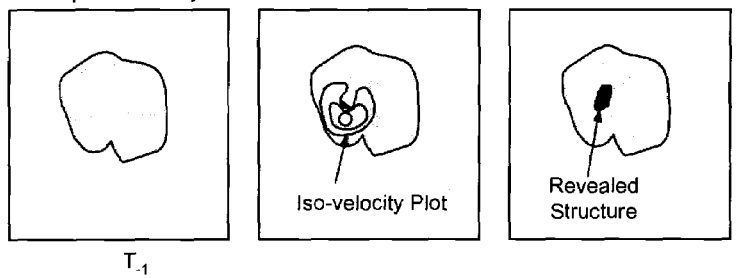
FIG. 6

A. Segmentation and Tracking Without Selective Activation
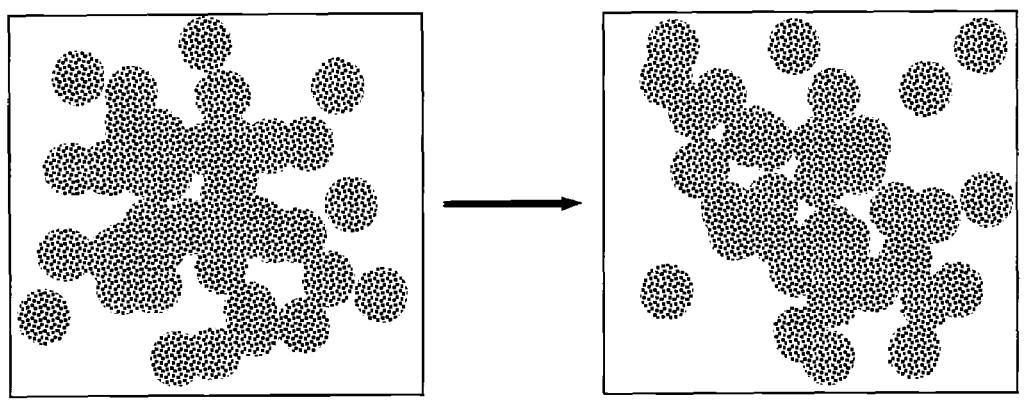
B. Segmentation and Tracking With Selective Activation
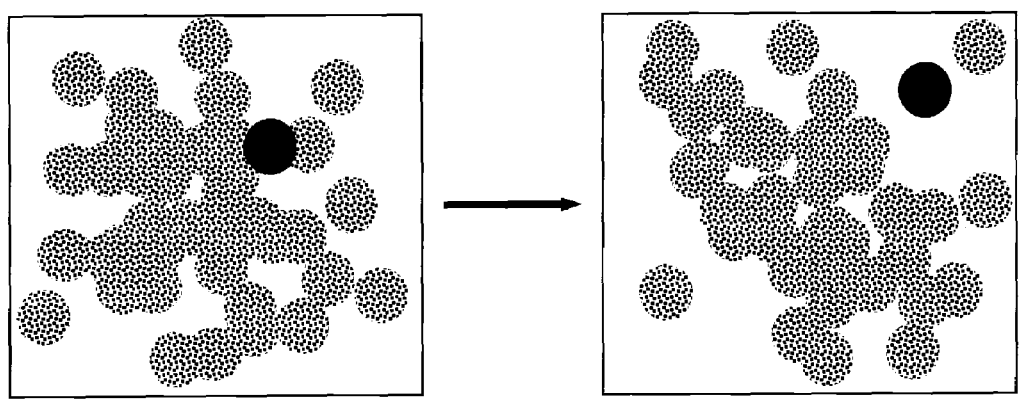
FIG. 10

Protein A with Variant "G" of GFP
490 nm Excitation
510 nm Emission
Protein B with Variant "Y" of GFP
510 nm Excitation
530 nm Emission
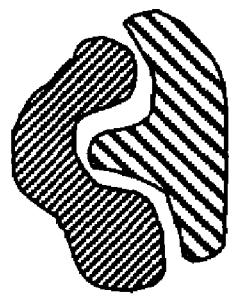
A/B FRET Pair Complex
490 nm Excitation
530 nm Emission
FIG. 11

SYSTEM AND METHOD EMPLOYING PHOTOKINETIC TECHNIQUES IN CELL BIOLOGY IMAGING APPLICATIONS

CROSS-REFERENCE TO RELATED APPLICATIONS

The present application is a continuation of U.S. patent application Ser. No. 10/872,329, filed Jun. 18, 2004, entitled "SYSTEM AND METHOD EMPLOYING PHOTOKINETIC TECHNIQUES IN CELL BIOLOGY IMAGING APPLICATIONS" which is allowed and claims the benefit of U.S. provisional application Ser. No. 60/480,432, filed Jun. 19, 2003, entitled "APPLICATIONS OF PHOTOKINETICS IN CELL BIOLOGY." The present application is also related to U.S. patent application Ser. No. 10/389,269, filed Mar. 13, 2003, entitled "MULTI-AXIS INTEGRATION SYSTEM AND METHOD," which issued as U.S. Pat. No. 7,283,253. The disclosures of the foregoing applications are hereby incorporated herein by reference in their entirety.

FIELD OF THE INVENTION

Aspects of the present invention relate generally to the field of cell biology, and more particularly to a system and method employing photokinetic techniques in various cell biology imaging applications.

BACKGROUND

Living matter is defined by more than the chemistry that governs the matter. Indeed, if one were to take the components of living matter (e.g., proteins, fats, sugars, nucleic acids, ions, etc.) and combine those components ex vivo, one would not reconstitute or otherwise create life. In fact, these components would generally tend to decompose into more base elements due to entropy. In that regard, living matter may be distinguished from the sum of its components by its ability to acquire energy and to employ that energy in defeating entropy. Specifically, cells are capable of creating individual or discrete compartments in which differing or unique chemical environments (e.g., ionic, pH, etc.) are maintained. These successive compartments establish and maintain specialized environments in which ordinarily unfavorable chemical reactions become permissible. Living matter "defeats" entropy most often by moving chemical reactions from compartment to compartment, using the individual compartments to create order out of chaos. Thus, life is distinguished from inorganic matter in that living matter is capable of employing energy to construct order (such as proteins) from otherwise disorganized building blocks (such as amino acids). In practice, an analysis of cell dynamics is essential in developing an understanding of cell biology.

Various methodologies have been developed to study cell dynamics. One of the more widely studied developments in this field involves the discovery of a protein from Aequorea victoria, a jellyfish that populates the Puget Sound region of Washington State. This protein is one of many found to fluoresce when exposed to deep blue light; this particular protein from Aequorea victoria is known as Green Fluorescent Protein (GFP) because green light (e.g., in a range generally centered around a wavelength of approximately 510 nm) is emitted when the protein is illuminated with deep blue light (e.g., in a range generally centered around a wavelength of approximately 410 nm).

As is generally understood in the art, GFP has a characteristic known as "self-assembly," i.e., it will self-assemble into a fluorescent form, even when expressed as protein chimera with mammalian proteins in mammalian cells. This means that new proteins can be created where the GFP protein is merely a continuation of a native protein. This new protein complex (the chimera) is fluorescent and permits the visualization of the native protein in its native environment.

Since the discovery of GFP, molecular biologists have succeeded in creating variants of the GFP protein, further optimizing its application in the study of mammalian cells. One such variant of GFP includes a modification of the absorption properties of the protein so that it is optimally excited by light having a wavelength of approximately 488 nm. Another notable modification to GFP involved creation of a variant that is only weakly fluorescent until it is activated by exposure to deep blue light having a wavelength of around 413 nm; once activated at this wavelength, the GFP variant becomes about one hundred times more fluorescent (488 nm excitation, 510 nm emission) than it was prior to activation.

Conventional technology is deficient at least to the extent that a system and method have yet to be designed that are operative in concert with, and take optimum advantage of, this photoactivated GFP (PA-GFP).

SUMMARY

Aspects of the present invention overcome the foregoing and other shortcomings of conventional technology, providing a system and method employing photokinetic techniques in various cell biology imaging applications. In that regard, it will be appreciated that the term "photokinetic" in this context generally refers to a characteristic or measurement related to or indicative of changes in one or more aspects of a chemical reaction, or to changes in the physical or chemical characteristics of material, responsive to excitation light. For example, change in rate of a chemical reaction, alteration of movements or dispersion of motile organisms, and other quantifiable responses may be attributable to incident electromagnetic energy of a particular frequency and wavelength. The "photokinetic" responses may be measured in accordance with the systems and methods set forth herein.

In some exemplary embodiments, a method of acquiring image data of an object comprises: selectively inducing photoactivation of material at a site on the object; performing an optical axis integration scan; simultaneously executing a time delay integration scan sequence; and selectively repeating the performing and the executing. The selectively inducing may generally comprise tagging the object to be scanned with a Green Fluorescent Protein variant.

As set forth in more detail below, the performing may comprise acquiring image data of the object at an image plane positioned along an optical axis, and may further comprise providing relative translation along the optical axis of the object and the image plane. Similarly, the executing may comprise providing relative translation along a lateral axis of the object and the image plane. In accordance with some embodiments, the performing further comprises selectively alternating a direction of the relative translation along the optical axis.

In some time delay integration scan sequences, the executing comprises synchronizing the relative translation along the lateral axis with a data acquisition rate associated with an imaging device. In some optical axis integration scans, the performing further comprises integrating the image data concomitantly with the acquiring. Embodiments of the disclosed methods may additionally comprise debluffing the image data subsequent to the integrating, deconvolving the image data subsequent to the integrating, or both.

In accordance with some aspects of the present disclosure, exemplary embodiments of a method of identifying a cellular structure may comprise: selectively inducing photoactivation of material at a site on the cell; observing dispersion of material activated responsive to the selectively inducing; and responsive to the observing, analyzing wave-front propagation to identify a cellular structure. The selectively inducing may generally comprise activating a Green Fluorescent Protein variant. Further, the selectively inducing generally comprises delivering excitation illumination having a selected wavelength. In some embodiments, the delivering may comprise pulsing the excitation illumination, and may additionally comprise selectively repeating the pulsing.

The observing may generally comprise utilizing using wide-field imaging. In some embodiments described with particularity below, the observing comprises performing an optical axis integration scan and simultaneously executing a time delay integration scan sequence.

The analyzing may comprise application of a Fourier Transform; additionally or alternatively, the analyzing may comprise calculation of iso-velocity values from successive images of wave-front propagation. In accordance with some embodiments, the analyzing comprises quantification of anisotropic flow; in one specific embodiment, the quantification identifies the cellular structure.

In accordance with some exemplary embodiments, a method of analyzing a biomolecule comprises: inducing photoactivation of material at a site on the biomolecule; photobleaching material at the site on the biomolecule; responsive to the inducing and the photobleaching, observing bound material that is not diffusing within the biomolecule; and responsive to the observing, identifying a compartmental structure of the biomolecule. Again, the inducing generally comprises activating a Green Fluorescent Protein variant.

As set forth in more detail below, one of the inducing and the photobleaching may comprise selectively pulsing excitation illumination having a predetermined wavelength. In one embodiment, each of the inducing and the photobleaching respectively comprises selectively pulsing excitation illumination having a respective predetermined wavelength. The photobleaching may allow minimization of background signal for the observing.

The observing may comprise utilizing using wide-field imaging; in particular embodiments set forth below, the observing comprises performing an optical axis integration scan and simultaneously executing a time delay integration scan sequence.

The identifying may comprise determining biomolecular transport into cellular organelles; additionally or alternatively, the identifying may comprise determining biomolecular transport into cellular compartments.

The foregoing and other aspects of the disclosed embodiments will be more fully understood through examination of the following detailed description thereof in conjunction with the drawing figures.

BRIEF DESCRIPTION OF THE DRAWINGS

FIG. 6 is a simplified diagram illustrating aspects of wave front dispersion analysis.

FIG. 10 is a simplified diagram illustrating one embodiment of photoactivation having utility in segmentation analyses.

FIG. 11 is a simplified diagram illustrating one embodiment of photoactivation having utility in methods of measuring molecular proximity using fluorescence resonance energy transfer.

DETAILED DESCRIPTION

Figure 1A:
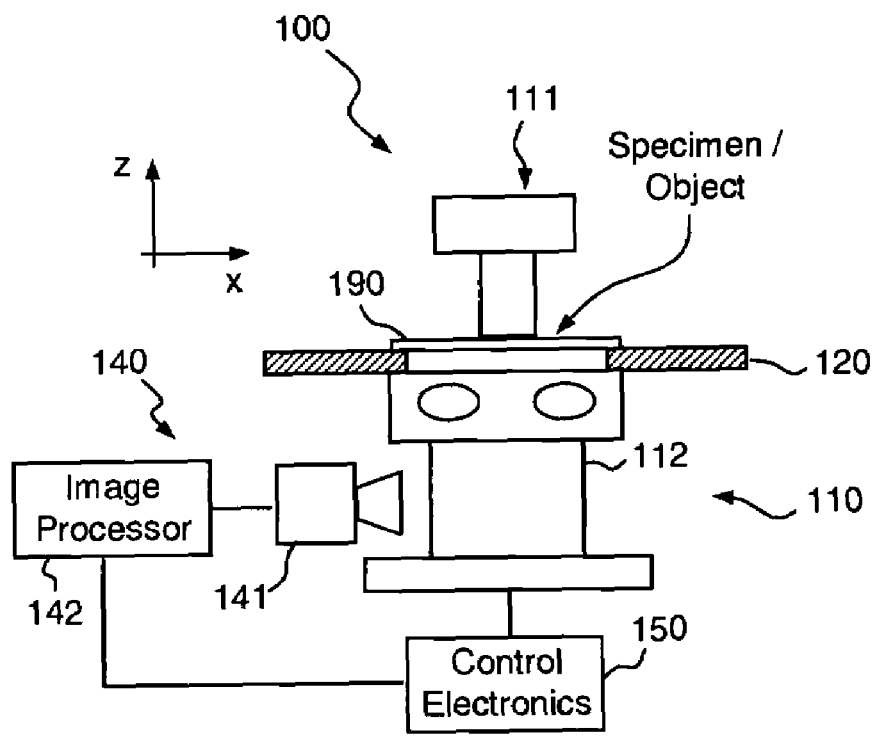
FIG. 1A is a simplified functional block diagram illustrating one embodiment of an image acquisition system operative in accordance with the present disclosure.

Initially, it is noted that aspects of the disclosed embodiments are variously directed to techniques involving time delay integration of temporal events, image acquisition using optical axis integration, or both. In that regard, systems and methods of time delay integration (TDI) and optical axis integration (OAI) are set forth in more detail in U.S. patent application Ser. No. 10/389,269, filed Mar. 13, 2003, entitled "MULTI-AXIS INTEGRATION SYSTEM AND METHOD," the disclosure of which is hereby incorporated herein by reference in its entirety.

Relevant portions of the foregoing application are reproduced below. In particular, it has been shown that a charge-coupled device (CCD) camera, a complementary metal oxide semiconductor (CMOS) detector, or similar apparatus employed in conjunction with an imaging system may be read row-by-row in concert with stage or sample movement in order to optimize acquisition rates. As set forth in more detail below, a similar methodology may be employed to capture fast temporal events in a spatially invariant setting. By way of example, a laser may be used to illuminate a small area on the sample or other field to be imaged; a single point detector, such as a photomultiplier tube (PMT), for example, may have utility in recording light intensities from the illuminated region. Additionally, the point detector may be repositioned over the surface of the object to record signals from the entire image plane. Further, a three-dimensional (3D) optical plane may be limited to an individual image plane by employing confocal apertures.

In that regard, it will be appreciated that image acquisition throughput often represents the rate-limiting factor in systems and methods of scanning high-content and high-throughput assays common in biomedical, cell biology, and other applications. Image acquisition throughput can be especially problematic when an assay requires detection of fluorescent probes, for example, and when high lateral resolution (in the x and y dimensions) is required for high-content image analysis algorithms. In cases where the detected signal is weak, such as in fluorescence imaging, for example, high numerical aperture (NA) lenses are generally used to maximize collection efficiency and to minimize exposure time. A side effect of high NA lenses, however, is that the depth-of-field (DOF, or the dimension of the in-focus region measured in the z direction) is very shallow. As a consequence, high NA lenses have limited ability to view thick objects, and are unable to follow uneven substrates without refocus.

Even in cases where the detected signal is strong or is otherwise easily acquired (such as transmitted visible light, for example) optical systems can still perform inadequately if the sample thickness is greater than can be imaged by the optical DOF; additional imaging difficulties can be introduced if the object to be imaged is not located in a plane orthogonal to the optical axis. These optical limitations often lead to the use of autofocus technology, or the need to acquire images at more than one focal plane.

Although much effort has been invested in autofocus technologies, optical axis integration techniques are more cost effective and generally provide improved performance in many scanning applications. The scanning techniques set forth in detail below are very tolerant of objects having inconsistent or variable focal planes, for example, and may be used to image thick objects. Additionally, scans performed in accordance with the present disclosure may be faster than those implementing autofocus or optical sectioning procedures.

Optical Axis Integration

A system and method operative in accordance with the present disclosure employ optical axis integration (OAI) techniques as set forth in detail below. For a particular object to be imaged, for instance, rather than attempting to determine a particular focal plane for optics or an imaging apparatus (i.e., precisely determining an appropriate or optimal z position of the image plane), the object may be scanned along the optical axis while a detector, computer, or other computational apparatus concomitantly integrates the acquired images or image data. The resulting image is an integral (i.e., projection) of the image of the three-dimensional (3D) object along the optical axis. That is, an OAI image may generally be expressed as follows:

$$i'(x,y) = \int_{-\infty}^{+\infty} i(x,y,z) dz \qquad 1$$

where i' is the two-dimensional (2D) projection of a 3D image, i, along the optical axis (z direction).

In this context, the 3D image, I, can be described mathematically as the object (o) of interest convolved with the point-spread-function (PSF) of a microscope or other optical apparatus, as follows:

$$i(x,y,z) = \int_{-\infty}^{+\infty} \int_{-\infty}^{+\infty} \int_{-\infty}^{+\infty} o(x',y',z') psf(x-x',y-y',z-z') dx'dy'dz' \qquad 2$$

Inserting equation 2 into equation 1 gives $$i'(x,y) = \int_{-\infty}^{+\infty} \int_{-\infty}^{+\infty} \int_{-\infty}^{+\infty} \int_{-\infty}^{+\infty} o(x',y',z') psf(x-x',y-y',z-z') dx'dy'dz'dz \qquad 3$$

Rearranging the integration along the optical axis, z, then yields $$i'(x,y) = \int_{-\infty}^{+\infty} \int_{-\infty}^{+\infty} \int_{-\infty}^{+\infty} o(x',y',z') \int_{-\infty}^{+\infty} psf(x-x',y-y',z-z') dz \, dx'dy'dz' \qquad 4$$

which is equivalent to $$i'(x,y) = \int_{-\infty}^{+\infty} \int_{-\infty}^{+\infty} \int_{-\infty}^{+\infty} o(x',y',z') \int_{-\infty}^{+\infty} psf(x-x',y-y',z) dz \, dx'dy'dz' \qquad 5$$

Rearranging the integration along z', the OAI image, I'(x,y), may be expressed as:

$$i'(x,y) = \int_{-\infty}^{+\infty} \int_{-\infty}^{+\infty} \int_{-\infty}^{+\infty} o(x',y',z') dz' \int_{-\infty}^{+\infty} psf(x-x',y-y',z) dz \, dx'dy' \qquad 6$$

Equation 6 shows that an OAI image, I'(x,y), may be expressed as the convolution of the integral of the object along the optical axis with the integral of the PSF along the optical axis. Equation 6 is also illustrative of the relationship between the projection of the object, the projection of the image, and the projection of the PSF along the optical axis.

The following definitions may facilitate further simplification of the foregoing formulation:

$$o'(x,y) = \int_{-\infty}^{+\infty} o(x,y,z) dz$$

$$psf'(x,y) = \int_{-\infty}^{+\infty} psf(x,y,z) dz \qquad 7$$

Inserting the definitions expressed above into Equation 6 yields $$i'(x,y) = \int_{-\infty}^{+\infty} \int_{-\infty}^{+\infty} o'(x,y) psf'(x-x',y-y') dx'dy' \qquad 8$$

The best method of solving Equation 8 for o'(x,y) involves Fourier Transforms, and is a well known procedure. Applying a Fourier Transform to both sides of Equation 8 and applying the convolution theorem (see, e.g., Bracewell, 1986) results in the following relationship:

$$I'(u,v) = O'(u,v) OTF'(u,v) \qquad 9$$

Capital letters have been used to denote the Fourier Transform of the corresponding functions, and the Fourier Transform of the PSF has been replaced with the conventional term for its Transform, the optical transfer function (OTF). Rearranging terms and performing an inverse Fourier Transform then yields $$o'(x,y) = F^{-1}[I'(u,v)/OTF'(u,v)] \qquad 10$$

where $F^{-1}$ represents the inverse Fourier Transform.

Equation 10 describes an efficient method of calculating a 2D projection of an object from a projection of the image and a projection of the optical PSF. A single-step solution may work well with good quality images; for lower quality images, however, an iterative solution of Equation 10 may yield a more reliable result. See, e.g., the constrained iterative technique described by Agard et al. (David A. Agard and John W. Sedat, *Nature*, volume 302, 1984, pages 676 et seq.).

As described and contemplated in the present disclosure, a system and method may implement, incorporate, or comprise OAI techniques in either of two forms: digital; or analog. In embodiments incorporating or practicing digital OAI, for example, a series of images may be collected along the optical axis and then digitally summed to form I'(x,y). This summation may occur during or after the scan, i.e., it may not be necessary to save individual optical sections as discrete images or collections of image data. In analog OAI embodiments, for example, I'(x,y) may be generated by scanning the object along the optical axis while the image data are accumulated within a CCD camera, a CMOS detector, a PMT, or another type of detector. The integration may be performed in the imaging apparatus or detector and generally may result in only a single image, i.e., a single image may represent the entire depth of the object in the z direction along the optical axis.

Analog OAI may have particular utility with respect to operations involving scanning microarrays, for example, with CCD cameras, CMOS devices, or other detectors. A system and method employing analog OAI may eliminate or substantially reduce reliance upon sophisticated, time-consuming, and processor intensive autofocus procedures.

In many applications, analog OAI may provide a number of advantages over digital OAI and autofocus, especially for automated scanners. For example, as compared with digital OAI, the analog OAI embodiments: require substantially lower data collection and processor overhead; exhibit lower read noise; and exhibit lower photon noise for equivalent exposure times.

As compared with traditional autofocus systems, advantages of the analog OAI embodiments may include the following: faster scan times; lower total exposure requirements; minimization or elimination of problems related to determining an arbitrary plane of focus; and integration of the 3D object yields or allows full quantitation of the object, i.e., the information content of the OAI image is higher than that achieved with autofocus systems, and accordingly, fewer structures associated with the object of interest are missed.

As compared with the analog technology, advantages of digital OAI embodiments may include a potential for achieving substantially larger photon counts; accordingly, 3D images may be made available for advanced image analysis such as 3D deconvolution, volumetric measurements, and the like.

The synergistic combination of the OAI techniques described above with deconvolution, for example, may provide a significant advance for automated slide scanning techniques. For instance, OAI images generally may benefit from the quantitative deblurring procedure; similarly, deconvolution performance may be improved because Equation 10 deals with images in 2D rather than 3D. Furthermore, many forms of image analyses based upon images obtained from autofocused systems will work equally well (or better) with projected images.

For example, a basic object detection operation may benefit from OAI image processing techniques; in that regard, it will be appreciated that images with minimal DOF (i.e., autofocus images) are less likely to contain a specific object of interest than the corresponding projection image. Likewise, analyses that use intensity integration may also benefit from application of OAI techniques, at least because the z dimension (i.e., along the optical axis) is already integrated into the OAI result. By way of another example, assays that integrate intensities within 3D structures (e.g., nucleus, cytoplasm, and endoplastic reticulum) may generally be more accurate with OAI images because 2D autofocus images cannot properly measure out-of-focus intensities.

Figure 1B:
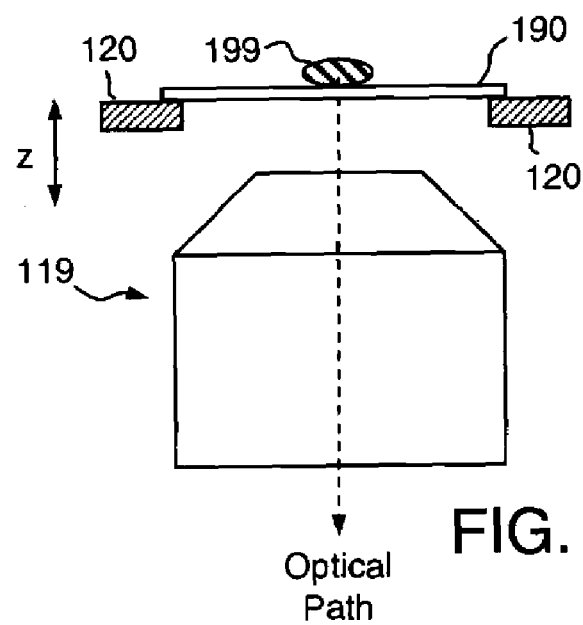
FIG. 1B is a simplified functional block diagram illustrating a portion of the image acquisition system depicted in FIG. 1A.

Turning now to the drawing figures, FIG. 1A is a simplified functional block diagram illustrating one embodiment of an image acquisition system operative in accordance with the present disclosure, and FIG. 1B is a simplified functional block diagram illustrating a portion of the image acquisition system depicted in FIG. 1A. Those of skill in the art will appreciate that FIGS. 1A and 1B are provided by way of example only, and that the specific arrangement of components is susceptible of numerous modifications; the exemplary scale, orientation, and interrelationship of the various components may be altered in accordance with system requirements. Additionally, as will become apparent from examination of the following description, some or all of the functionality of some components depicted as discrete elements may be combined or incorporated into other components.

System 100 generally comprises a microscope 110 operably coupled to a precision movable stage 120 and to an image acquisition component 140; stage 120 may be configured and operative to support a microarray, microscope slide, or other similar structure (reference numeral 190) upon which a specimen or object 199 to be imaged is disposed. As is generally known in the art, microscope 110 may comprise, or be operative in conjunction with, an illumination source 111 for illuminating stage 120, slide 190, or both with light of a predetermined or selected frequency or spectral bandwidth; in that regard, illumination source 111 may provide light in the visible, infrared, or ultraviolet wavelengths.

In some embodiments, illumination source 111 may be incorporated within housing 112 of microscope 110, i.e., on the opposite side of stage 120 and slide 190 than depicted in FIG. 1A. Alternatively, an additional source of illumination (not shown) to be used in conjunction with, or in lieu of, source 111 may be accommodated or maintained in housing 112. In these embodiments, any such illumination source disposed within housing 112 may be suitably dimensioned and positioned neither to interfere with optical components of microscope 110 nor to obstruct the optical path through microscope 110 (to image acquisition component 140).

As noted above, stage 120 may be movable relative to optics (e.g., objective 119 illustrated in FIG. 1B) incorporated into microscope 110 (microscope optics are not depicted in FIG. 1A). In some embodiments, stage 120 may be movable in both the x and y directions (where the y axis is normal to the plane of FIGS. 1A and 1B). In this context, both the x axis and the y axis may generally be referred to herein as "lateral" axes, and may describe a plane orthogonal to the optical axis (described below) of system 100. Additionally or alternatively, stage 120 may incorporate or comprise one or more structures and mechanisms configured and operative precisely to position slide 190 laterally in the x and y directions relative to the structure of stage 120 itself. In such embodiments, precise 2D lateral positioning (i.e., x and y coordinates) of object 199 relative to the optical path of microscope 110 may be achieved through movement of stage 120 relative to microscope optics, movement of slide 190 relative to stage 120, or both.

In some embodiments, stage 120 may also be movable along the z axis (the optical axis). It will be appreciated that microscope optics may also facilitate positioning an object on slide 190 in the proper location in 3D space (i.e., x, y, and z coordinates) relative to the optical path and the focal point of objective 119. In that regard, one or more optical components of microscope 110 such as objective 119 may be movable in the z direction, either in addition to, or as an alternative to, selectively moving stage 120 along the optical axis. Additionally or alternatively, objective 119 may be movable along the x axis, the y axis, or both.

It will be appreciated that numerous mechanisms and methods of positioning object 199 to be imaged relative to microscope optics are generally known. Relative movement of various components (such as slide 190, stage 120, and objective 119, for example), either individually or in combination, may vary in accordance with system requirements and configuration, and may be effectuated to position object 199 in a suitable location relative to objective 119. The present disclosure is not intended to be limited by the structures and processes employed to position object 199 relative to objective 119 and the optical path or the image plane. Accordingly, reference made herein to relative motion of object 199 and an image plane may generally comprise movement of object 199, movement of the image plane, or some combination of both.

Microscope optics may generally be configured and operative in conjunction with image acquisition component 140; in that regard, component 140 generally comprises a camera, a CCD imager, a CMOS device, a PMT, or some other detector 141 operably coupled to an image processor 142 or other appropriate electronics. System 100 may additionally include control electronics 150 operative to control, for example: operational parameters, functional characteristics, or other configurable aspects of image processor 142 and detector 141; two- or three-dimensional motion of stage 120, objective 119, or other components; power output, spectral bandwidth, frequencies, or other parameters for source 111 and any other illumination source incorporated into system 100; data storage; and the like. In that regard, electronics 150 may comprise one or more microprocessors, microcontrollers, or other programmable devices capable of executing computer readable instructions; additionally, electronics 150 may also comprise or be operably coupled with data storage media or networked devices such as file servers, application servers, and the like. Those of skill in the art will appreciate that various methods and apparatus employing microprocessors or computer executable instruction sets to configure and to control operation of image acquisition systems are generally known.

In operation, image data acquired by detector 141 may be summed, manipulated, saved, or otherwise processed by hardware, software, or both resident at image processor 142; in some embodiments, functionality of processor 142 may be influenced or controlled by signals transmitted from electronics 150 as noted above. Alternatively, the functionality of image processor 142 and electronics 150 may be incorporated into a single device, for example. Specifically, image processor 142 may be operative in accordance with instruction sets to compute solutions or approximations for the equations set forth herein.

Figure 2A:
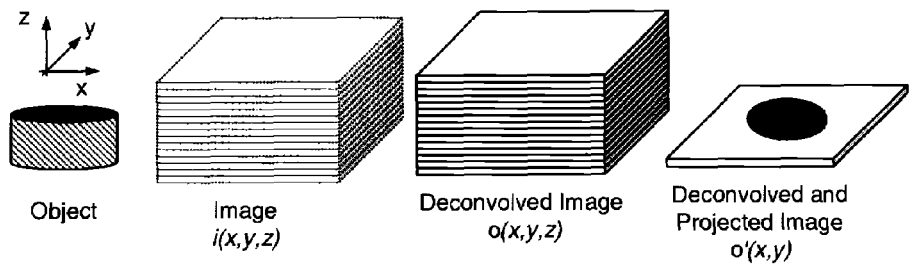
FIGS. 2A and 2B are simplified diagrams illustrating the general operation of embodiments of image acquisition and image data processing methods.
Figure 2B:
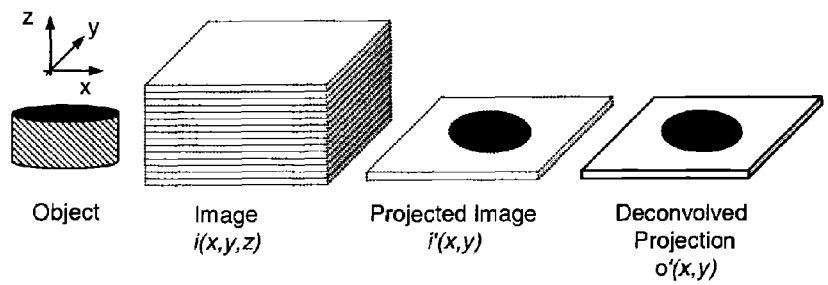
Figures 3A, 3B:
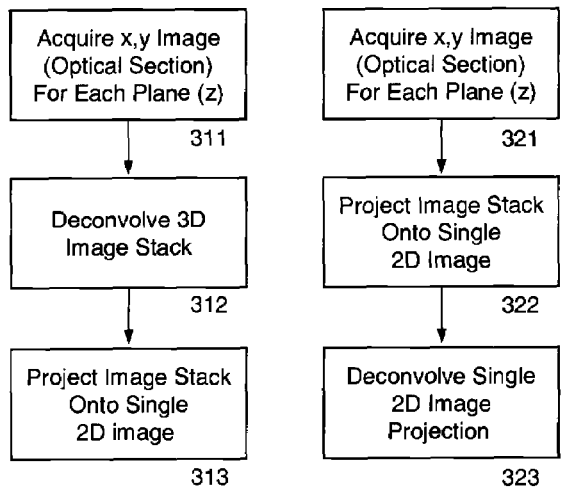
FIGS. 3A and 3B are simplified flow diagrams illustrating the general operation of the methods depicted in FIGS. 2A and 2B.

FIGS. 2A and 2B are simplified diagrams illustrating the general operation of embodiments of image acquisition and image data processing methods, and FIGS. 3A and 3B are simplified flow diagrams illustrating the general operation of the methods depicted in FIGS. 2A and 2B.

FIGS. 2A and 3A generally illustrate one conventional approach to image processing operations. As indicated at block 311, a series, or stack, of 2D images is acquired in sequential x,y planes (i.e., optical sections) along the z axis. The resulting image, i(x,y,z), is expressed mathematically at Equation 2 above, which is computationally expensive to solve. As illustrated in FIG. 2A, the deconvolution operation depicted at block 312 is executed with respect to the entire stack of optical sections, and is accordingly inefficient and processor-intensive; since each optical section includes data from other sections (due to DOF range, for example), the deconvolution operation processes more data than required. Finally, the deconvolved 3D image is projected into 2D image, o'(x,y), as indicated at block 313.

FIGS. 2B and 3B generally illustrate a significantly improved approach to image processing operations as contemplated herein. As in the FIG. 3A embodiment, a series, or stack, of 2D images may be acquired in sequential x,y planes (i.e., optical sections) along the z axis (block 321). The resulting image, i(x,y,z), is expressed mathematically at Equation 2 above, which is computationally expensive to solve. As illustrated in FIG. 2B and indicated at block 322, the stack of optical sections may be projected into 2D image, I'(x,y), prior to deconvolution; this image is expressed mathematically at Equation 8 above, which is a substantially simplified, 2D version of Equation 2. The deconvolution operation depicted at block 323 results in the same 2D image, o'(x,y), as the embodiment described above with reference to FIGS. 2A and 3A; the FIG. 3B embodiment generates the deconvolved projection at a significant savings in computational overhead, however, since the processor-intensive deconvolution is executed in only two dimensions.

Time Delay Integration

As used herein, the phrase "time delay integration" (TDI) generally represents a method of continuous scanning which may be implemented in conjunction with CCD cameras, CMOS devices, PMT apparatus, or other imaging devices. In CCD cameras and similar apparatus, for example, incident light creates electric charge at individual charge-coupled wells on the device surface. Charged electrons are then transferred sequentially down the columns of the chip (parallel shifts) while the row that reaches the bottom of the chip is transferred to an accumulator called the serial register. The serial register is then shifted horizontally and processed by an A/D converter.

In accordance with some TDI embodiments, precision motion control may be employed to synchronize motion of the object being imaged or motion of the camera or other imaging device (as set forth above with reference to FIG. 1A) with motion of the charged electrons across the CCD or imaging device surface. Relative translation of the object and the image plane along the lateral axis may be controlled such that a particular portion of the imaged object tracks down the chip as the electrons representing that particular portion of the image are shifted down the chip. As set forth in detail above, such relative translation may comprise motion of the object, motion of the image plane, or both. Accordingly, the object may be continuously imaged as it passes down the chip. TDI methodologies may facilitate or enable efficient scanning of, among other things, fluorescent DNA microarrays, for example, and may have utility in various other applications related to scanning myriad biological specimens.

Figure 4:
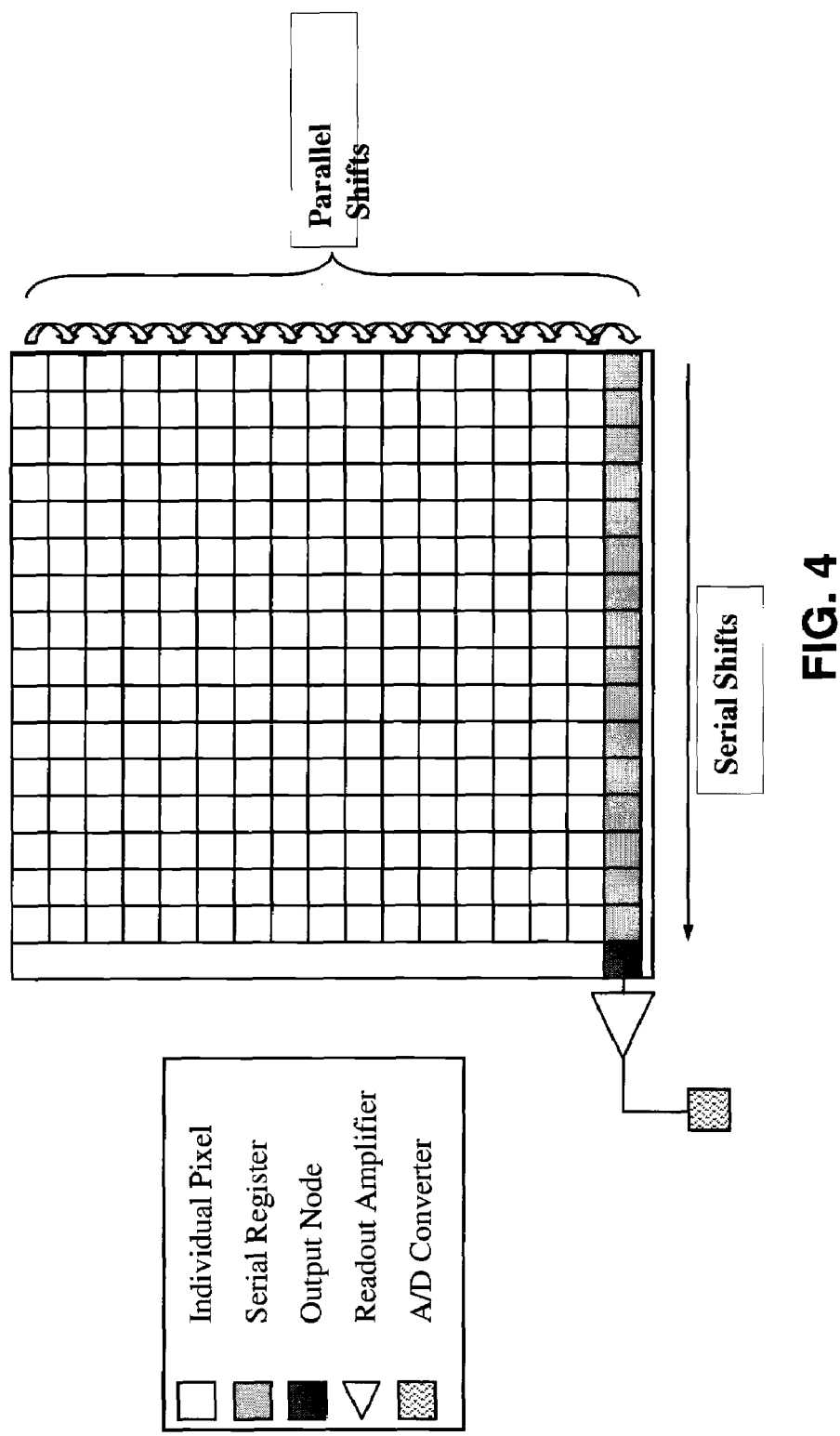
FIG. 4 is a simplified diagram illustrating the general operation of shifts and readout functionality for a full frame CCD camera.

FIG. 4 is a simplified diagram illustrating the general operation of shifts and readout functionality for a full frame CCD camera. In that regard, FIG. 4 provides a simple demonstration of slow-scan CCD camera read operations. Individual pixel electrons are shifted in parallel (e.g., down the columns to successive rows) to a predetermined portion of the chip (e.g., the bottom of the chip in FIG. 4). Image data at the bottom row are shifted off of the chip onto the serial register, which is, in turn, shifted horizontally to the readout amplifier to create a voltage that is digitized to form a digital image.

It will be appreciated that the FIG. 4 embodiment is provided for illustrative purposes only, and that various CCD cameras, CMOS devices, PMT apparatus, or other imaging devices may be characterized by alternative operational features, particularly with respect to the exemplary geometry. For example, the operation of some CCD cameras may execute parallel shifts oriented at 90 or 180 degrees from those depicted in FIG. 4.

Figure 5:
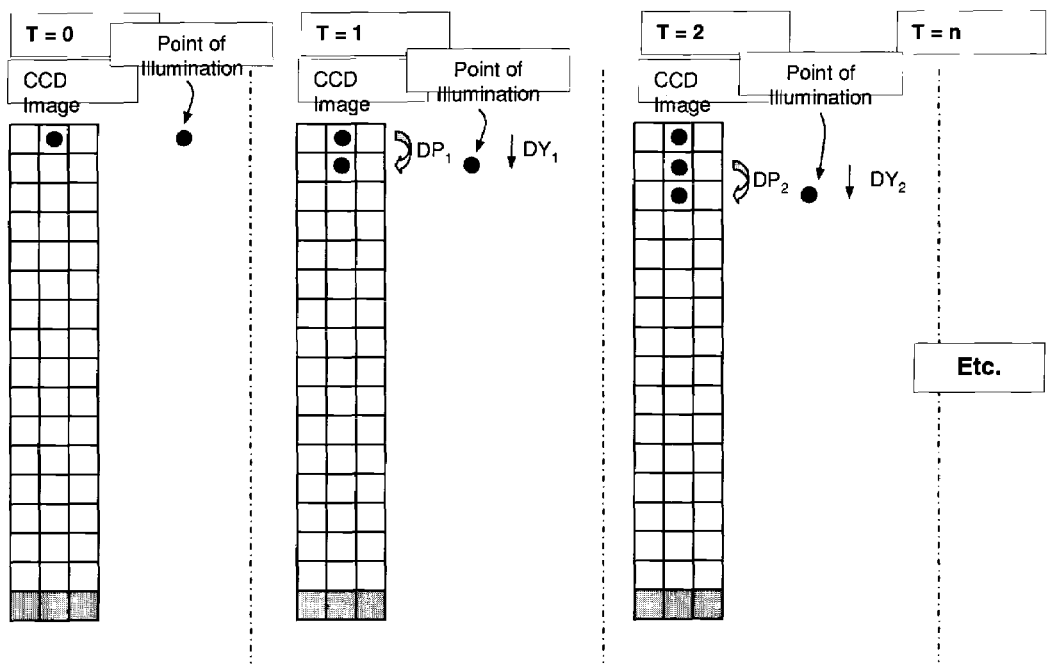
FIG. 5 is a simplified diagram illustrating one embodiment of time delay integration synchronized with temporal events.

FIG. 5 is a simplified diagram illustrating one embodiment of time delay integration synchronized with temporal events. In that regard, FIG. 5 illustrates a precise motion control TDI implementation which may be employed in fluorescence imaging systems, for example, or in numerous other imaging applications. In accordance with the exemplary embodiments, a given location on the specimen ("point of illumination" in FIG. 5) may be moved (either relative to the imaging device, for example, or relative to the image plane of the system) in synchrony with the parallel shifts such that $V_P$ (i.e., the parallel shift velocity) is equal to $V_Y$ (i.e., the shift velocity of the point of illumination). In the foregoing manner, the specimen may be imaged throughout the period of time that it takes for an entire chip to be read by the camera.

In this context, synchronous motion between the object and the CCD row may be effectuated substantially as set forth in detail above with reference to FIG. 1A. Relative motion of slide 190, stage 120, various optical components, or some combination thereof, for instance, may accurately position the point of illumination depicted in FIG. 5 in a suitable location for imaging during the scan. The degree of synchronicity, the velocities imparted to the mechanical components, the precision with which the object must be positioned for a desired imaging quality, mechanical settling time, backlash, and the like may vary in accordance with system configuration, and may be application dependent.

Upon examination of FIGS. 4 and 5, it will be readily apparent that relative translation of the object and the image plane along the lateral axis as set forth above may be synchronized with the rate at which data are acquired and read from the detector. Accordingly, it is noted that the capabilities of the imaging device (such as detector 141) and other components of the optical system (such as, inter alia: the maximum resolution and the time required to focus the imaging device; and NA and DOF of the optics) may affect the behavior and performance of the system employing the FIG. 5 TDI embodiment.

Consistent with the foregoing description, aspects of the present invention are related to use of row-by-row reading of a CCD, CMOS, PMT, or similar detector to facilitate fast sampling rates (as fast as approximately 1 ms or better, for example) of a single point, i.e., TDI reading of a CCD camera or other imaging device in conjunction with single point or single row (targeted) illumination techniques may enable fast acquisition of time-resolved data. This time-resolved information may be used for spectroscopic examination in such applications as Fluorescence Life-time Imaging, Fluorescence Recovery After Photobleaching, Photoactivation, Rotational Diffusion Measurements, and many other applications. Since the methodology may inherently be combined with traditional imaging, the same detector (whether based upon CCD, CMOS, or other technology) may be used to image an entire field (such as a cell) as well as for site-specific spectroscopic examination.

Analysis of Dispersion Wave-Fronts Subsequent to Photoactivation

FIG. 6 is a simplified diagram illustrating aspects of wave front dispersion analysis. Specifically: FIG. 6A is a simplified diagram illustrating simple isotropic dispersion from a single activation site; FIG. 6B is a simplified diagram illustrating anisotropic dispersion and depicting non-uniform impedance to diffusion vertically relative to horizontally; FIG. 6C is a simplified diagram illustrating the FIG. 6B dispersion quantified and converted into an iso-velocity plot; and FIG. 6D is a simplified diagram illustrating one embodiment of a method of uncovering hidden cellular structure employing iso-velocity plots and dispersion analysis.

Variants of PA-GFP have been used in conjunction with a confocal microscope for both activation and subsequent, i.e., post-activation, imaging. The confocal microscope previously employed was limited in the speed at which subsequent frames were acquired. Imaging limitations, in turn, inherently limit the temporal resolution of such instruments. In accordance with the present disclosure, however, rapid and non-isotropic (or "anisotropic") dispersion of protein chimeras may be observed using laser induced photoactivation and subsequent wide-field imaging. Such observation of anisotropic dispersion may facilitate detailed analysis of the flow patterns of proteins within cellular compartments and between those compartments. While complementary with fluorescence recovery after photobleaching experiments, this analysis is unique in that it is able to divulge patterns of flow from the activation site. Specifically, the use of anisotropic flow characteristics may reveal flow resistant structures within cells as indicated in FIG. 6D.

Additionally, aspects of the disclosed embodiments involve application of waveform or wave-front propagation analyses to the study of cellular structure. In some instances, these analyses may be embodied in or comprise construction of iso-velocity graphs of dispersion. In accordance with the present disclosure, an iso-velocity map may be considered analogous to a topographical map where the lines of equivalent velocity of dispersion are mapped instead of elevation. More complex analyses involving the Fourier Transform of these waveforms may reveal high-resolution maps of flow patterns within cells. As noted above, FIG. 6B is a simplified diagram illustrating anisotropic dispersion; non-uniform impedance to diffusion is represented by the flattened area of dispersion in the third and fourth panels in FIG. 6B. This anisotropic or non-uniform dispersion may be quantified subsequent to rapid wide-field imaging, some embodiments of which may employ one or more of the techniques set forth above. Iso-velocity plots, i.e., depicting contours representing locations where dispersion proceeds at substantially equivalent velocities, are illustrated in FIGS. 6C and 6D. As indicated in FIG. 6D, iso-velocity plot contours and wave-front dispersion analyses may facilitate identification of cellular structure that impedes dispersion.

Rapid Three-Dimensional Studies of Dispersion Subsequent to Photoactivation

Methodologies for rapidly acquiring images from 3D space using OAI techniques are disclosed in U.S. patent application Ser. No. 10/389,269, and set forth in detail above. These methods provide means of acquiring summary data of 3D volumes rapidly, and may be combined with photoactivation and photobleaching to achieve estimates of 3D anisotropic diffusion as well as 3D diffusion constants, even in rapidly diffusing substances. In that regard, FIGS. 2B and 3B illustrate the general operation of one embodiment of an image acquisition and image data processing method employing the principle of OAI.

Specifically, the FIG. 2B embodiment acquires a stack of 2D images in sequential x,y planes along the z axis. The resulting image, i(x,y,z), may be expressed mathematically in accordance with Equation 2 set forth above. The stack of optical sections may be projected into a 2D image, I'(x,y), prior to deconvolution; this image may then be expressed mathematically in accordance with Equation 8, generating a deconvolved projection at a significant savings in processing overhead.

As set forth above, an OAI method may involve collecting an extended focus image either through digital or analog integration. The extended focus image (optical axis integrated) may then be deconvolved digitally. The result of such acquisition and data processing is a high-resolution image that accurately represents the sum of image intensities across a large DOF. In some embodiments, OAI may be implemented in concert with moving the stage (or the optics, or both) laterally, as in TDI methodologies, so as to acquire a large field of view with high lateral resolution as well as a large DOF.

It will be appreciated that a combination of OAI and TDI imaging techniques may have particular utility in the post-activation wave-front propagation analyses set forth above with reference to FIG. 6. Specifically, in accordance with some embodiments, a method of acquiring image data of an object may comprise: selectively inducing photoactivation of material at a site on the object; performing an optical axis integration scan; simultaneously executing a time delay integration scan sequence; and selectively repeating the performing and the executing to image the object and, optionally, to acquire wave-front propagation data.

Unidirectional Diffusion and Flow

Most models of diffusion and flow within living organisms assume that diffusion is bidirectional. The classic models assume that the mixing of chemical species proceeds randomly from a heterogeneous distribution to a homogeneous distribution. These assumptions are justified, in part, because they make many calculations much simpler and, in part, because methods to test alternative hypotheses have heretofore been unavailable. One way that these assumptions may be tested is by activating a pool of PA-GFP tagged protein and subsequently, before the pool is homogeneously distributed within the cell or compartment, depleting the remaining activated population at the activation site. If diffusion is truly bidirectional, the depleted site at the center of the activation will fill back in at the same rate as the leading edge of the diffusion away from the activation site. If structures that create non-uniform diffusion exist, then the foregoing rates will differ.

The existence of such unidirectional channels may suggest that diffusion is controlled in ways that have yet to be considered within the cell. Such channels may be considered as playing an important role in disease processes such as bacterial invasion and compartmentalization. Additionally, control of such unidirectional flows should provide significant targets for pharmaceutical intervention and may be used for deriving new drug classes for antibiotics, antiviral agents, chemotherapeutics, and neuro-pharmaceutical agents.

Figure 7:
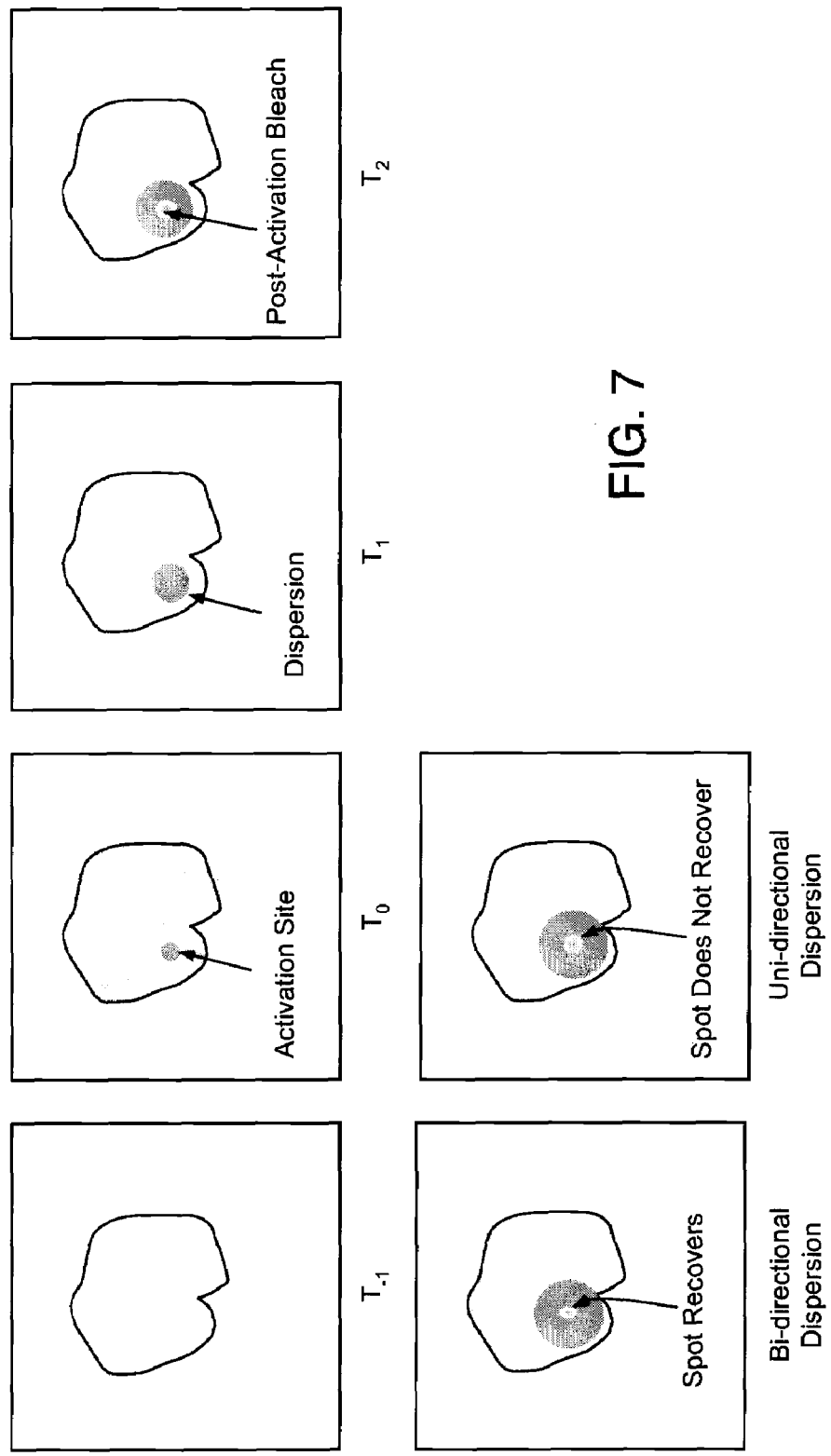
FIG. 7 is a simplified diagram illustrating one embodiment of a method of studying flow directionality.

FIG. 7 is a simplified diagram illustrating one embodiment of a method of studying flow directionality. A spot of light (electromagnetic energy having predetermined or desired frequency, wavelength, and intensity characteristics) may activate the PA-GFP (as indicated at time=$T_0$). The activated PA-GFP may then be allowed to disperse (as indicated at time=$T_1$). At time=$T_2$, the same site selected for activation may be photobleached, for example, using a 488 nm laser (other wavelengths may be employed, for instance, depending upon system requirements, the composition of the fluorescent compound, and other factors). The recovery of fluorescence may then be monitored at the bleach site. If the flow is bidirectional, then the bleach spot may be expected to recover (bidirectional dispersion). If the flow is unidirectional, on the other hand, the bleach spot may be expected not to recover (unidirectional dispersion).

Unidirectional Molecular Incorporation into Organelles

Organelles are compartmental structures within cells; the organelles represent the microenvironments that the cell uses to create so called "uphill" reactions, i.e., those reactions involved in the synthesis of molecular species that involve an increase in organization within the cell. Examination of the movement of proteins and biomolecules into and out of these compartments may facilitate understanding of protein dynamics. In some cases, however, the organellar transport is a small fraction of the total mass of biomolecule, rendering imaging and measuring the organellar fraction difficult.

In accordance with the present disclosure, however, a method of measuring this fraction is possible. For instance, PA-GFP attached to a biomolecule may be activated; following a predetermined "wait" period or duration, for example, a focused spot of light suitable for exciting the activated PA-GFP may be introduced away from the area of study, for instance, at a distal portion of the cell. The foregoing technique may effectively photobleach the "free" component of the PA-GFP biomolecule, eliminating it from the measurement. In some embodiments, the remaining fraction of the PA-GFP labeled biomolecule may be bound or compartmentalized. That remaining fraction may be studied without the interference of the mobile fraction.

Figure 8:
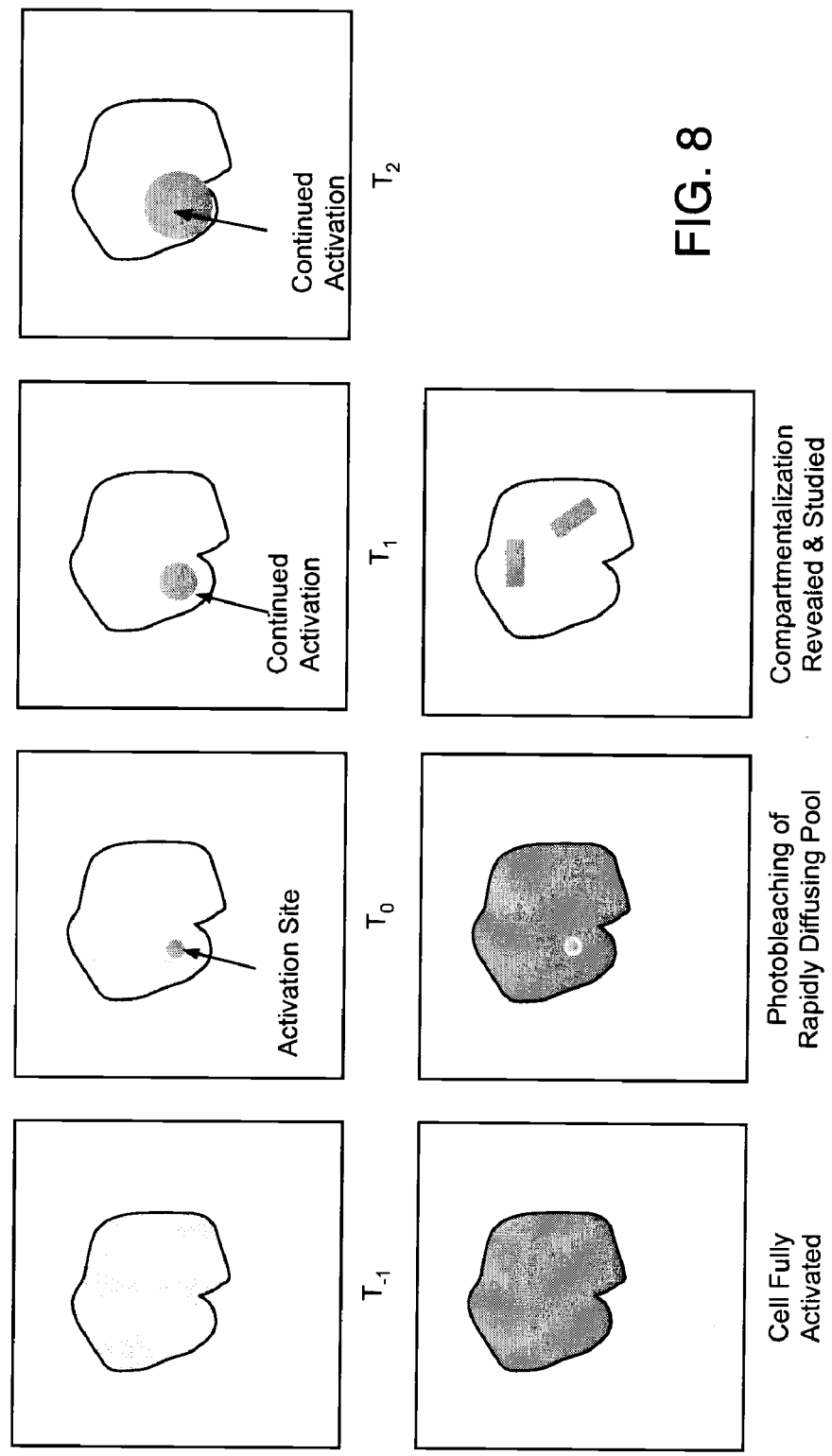
FIG. 8 is a simplified diagram of one embodiment of isolating a remaining fraction of a biomolecule tagged with a GFP variant.

In that regard, FIG. 8 is a simplified diagram of one embodiment of isolating a remaining fraction of a biomolecule tagged with a GFP variant. In the FIG. 8 embodiment, PA-GFP may be repeatedly activated until the cell is largely filled with activated PA-GFP; this repeated activation may be followed by repeated photobleaching until most or all of the freely diffusing PA-GFP is bleached. Compartmentalized or bound GFP that is not freely diffusing may be retained by the cell and used to visualize compartmental dynamics and to obtain measurements of compartmental characteristics.

Accordingly, a method of analyzing a biomolecule as set forth herein may comprise: inducing photoactivation of material at a site on the biomolecule; photobleaching material at the site on the biomolecule; observing bound material that is not diffusing within the biomolecule; and responsive to the observing, identifying a compartmental structure of the biomolecule.

Protein Lifetime Studies

Figure 9:
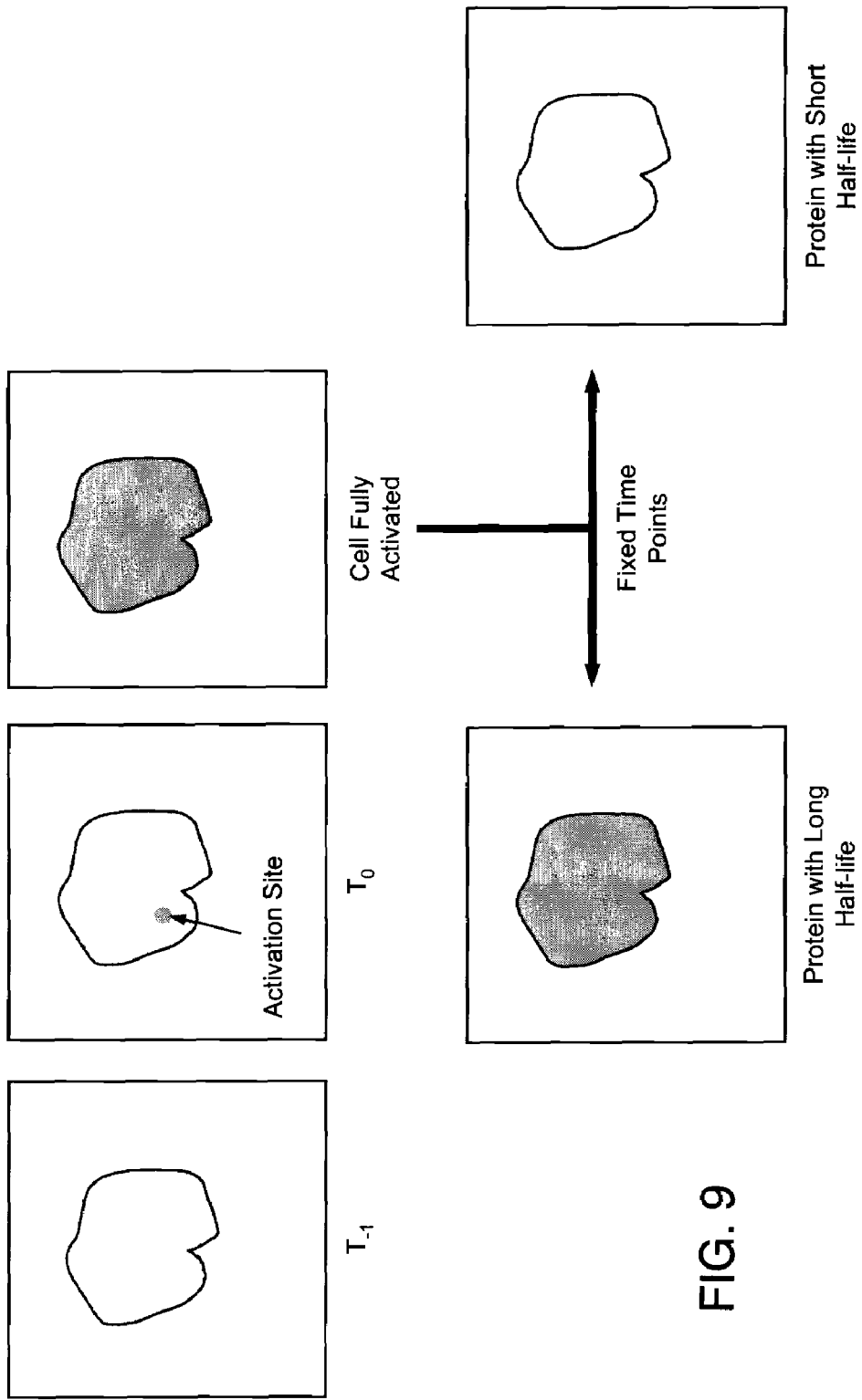
FIG. 9 is a simplified diagram illustrating in situ protein half-times.

One aspect of the study of biomolecules involves examination of what is conventionally characterized as the "turnover rate." In particular, the half-life of a molecule is especially important in some studies of receptor binding and effector molecules. As set forth in more detail below, aspects of the present invention involve methodologies relating to measuring biomolecule half times. In some exemplary embodiments, the protein may be photoactivated. Since the activation of PA-GFP involves a non-reversible reaction between two amino acids, the fluorescence itself is non-reversible. Thus, the fluorescence half-time is equal to the total loss of fluorescence over time minus the loss due to photobleaching and the variability of the illumination intensity. If the input or excitation illumination intensity is measured with a photosensor, and if the photobleaching fraction can be quantified, then the total change in fluorescence attributable to the protein half-life may readily be computed. In that regard, FIG. 9 is a simplified diagram illustrating in situ protein half-times.

Photoactivation of GFP to Aid Image Segmentation

Computer based imaging is facilitating the conversion of cell biology from a descriptive, or "qualitative," discipline to a quantitative discipline. In that regard, clear delineation or designation of the boundaries between cells, organelles, and their environments may have particular utility in quantitative cellular analyses. In order to facilitate such designations, computer algorithms have been created that seek to "segment" or otherwise to divide the image between those locations that fall within a given cell or structure and those that fall outside. In that regard, acquired signals may be quantified, for example, as a function of time, cell cycle, disease state, and so forth. The identification of those locations that fall within and without the cell and its structures may represent the most difficult of imaging tasks in many applications; the challenge is to identify structures with particularity (and to increase or amplify signals representative of the structures) while diminishing the signal of the background.

In accordance with the present disclosure, PA-GFP, either attached to organelle specific proteins or randomly expressed, may be employed to facilitate location and identification of particular cells or attendant structural components. The organellar regions may be activated by targeting the area under analysis with excitation illumination of an appropriate wavelength employing, for example, a light source generating light having a wavelength of approximately 413 nm. These organelles may then be clearly discernable from background signals based upon the presence of PA-GFP signal. This increased contrast (signal to background) may facilitate automated segmentation of the acquired image. Once the boundaries of the cell or organelle are delineated, other color channels may be used to mark proteins and structures of interest for subsequent quantification.

A variant of this methodology may be used in developmental biology. A critical methodology in the discipline of cell biology is the study of cell lineage, i.e., identifying controls and signals that may determine the fate of cells as the organism develops from a single or few-celled organism to maturity. Conventional cell lineages are difficult to perform and require hundreds of man-hours. In accordance with the present disclosure, individual cells in blastocysts and embryos may be marked by photoactivation. Since the activation of PA-GFP is non-reversible, these cells and their progeny will remain fluorescent until either the activated protein is sufficiently diluted out by non-activated protein or until the proteins are actively degraded by the cell. These activated cells may be followed automatically using one or more imaging techniques substantially as set forth above.

In that regard, FIG. 10 is a simplified diagram illustrating one embodiment of photoactivation having utility in segmentation analyses. As indicated at panel A in FIG. 10, individual cells may be difficult to delineate, and tracking one particular cell may be virtually impossible without the beneficial effects of selective photoactivation. As indicated at panel B in FIG. 10, however, one cell has been specifically marked by photoactivation. That individual cell, having been tagged in accordance with the procedure set forth above, may be much easier to separate optically from its neighbors for segmentation; additionally, movements over time are more easily observed.

Photoactivation of GFP in the Study of Fluorescence Resonant Energy Transfer (FRET)

Cellular activity is controlled by the interactions of biomolecules, most notably, proteins. In order for proteins to interact, they must generally be close to each other (typically within 5-10 Å) at distances which may be too small to measure directly with optical methods; methodologies other than optical techniques must generally be employed in that regard. One common technique for observing or otherwise monitoring biomolecule interactions is generally referred to as Fluorescence Resonant Energy Transfer, or "FRET." In accordance with conventional FRET techniques, two fluorescent molecules approach each other in close enough proximity that the excitation of one molecule (the "donor") yields fluorescent emission from the other (the "acceptor"). As is generally known in the art, this energy transfer is a quantum mechanical event that involves the sharing of energized electrons between the two molecules. In theory, the existence of FRET can be monitored, for instance, by exciting the donor and looking for emissions typical of the acceptor. In practice, however, it is difficult to know with certainty that the acceptor emission is actually caused by donor absorption and FRET influences, or whether it is an artifact of acceptor excitation and emission independent of FRET.

In accordance with the foregoing description, a method of FRET is enabled whereby the acceptor absorption and emission may be measured in the presence of the donor molecule, but without fluorescence of the donor molecule. Upon measuring the acceptor localization and intensities, the donor molecule (PA-GFP) may be initiated by activating the PA-GFP. At this point, enhancement of acceptor signal may be interpreted as due to the presence of the donor and FRET influences. The foregoing procedure may be used as a calibration or correction for FRET measurements. FIG. 11 is a simplified diagram illustrating one embodiment of photoactivation having utility in methods of measuring molecular proximity using fluorescence resonance energy transfer. Specifically, FIG. 11 demonstrates how the combination of two proteins, each having an appropriate fluorochrome attached, may yield a complex that exhibits FRET effects.

It will be appreciated that the foregoing methodologies are susceptible of myriad modifications and have utility in numerous applications. The description set forth above, for example, may enable efficient row-by-row reading of a CCD or similar apparatus in concert with single point or row illumination for fast data acquisition of time-resolved data; those of skill in the art will appreciate that the addition of a diffraction grating may enable utilization of substantially the entire length along a detector row for spectral information. As set forth above, the CCD or other imaging device may, additionally or alternatively, be used for traditional wide-field imaging processes.

In some embodiments, pulsed point activation and rapid wide-field imaging may be implemented to study dispersion characteristics of activated fluorescent materials. Specifically, the application of wave-front propagation analytical tools may enable detailed study of cellular structure; as set forth above, the application of Fourier Transforms may facilitate such investigations of wave-front propagation. In some embodiments, the calculation of iso-velocity values from successive images of wave-front propagation may have particular utility in photoactivation experiments. Such iso-velocity maps of wave-front propagation may be displayed independently, for example, or simultaneously (or otherwise in combination) with image intensity data.

Given the foregoing detailed description, multi-dimensional data acquisition techniques may be applied to the analysis of dispersion characteristics subsequent to photoactivation. Specifically, multiple axis integration methods, such as OAI and TDI, may facilitate data acquisition and enable detailed study of such dispersion.

In some embodiments, the combination of photoactivation and photobleaching techniques may be implemented to study anisotropic flow directions in cell biology. Such anisotropic flow evaluations may be implemented in conjunction with the study and testing of host invasion in cell biology, the development and testing of antibiotics using cell biology, the development and testing of antiviral agents using cell biology, the development and testing of chemotherapeutic agents using cell biology, the development and testing of neuro-pharmaceutics using cell biology, and other applications.

As described above, photobleaching procedures may allow or facilitate removal of background signal in the study of cellular structure. Specifically, application of photoactivation processes and subsequent photobleaching processes may be implemented for the study of biomolecular transport into cellular organelles and compartments, the study of biomolecular binding in cellular organelles and compartments, and other applications.

Based upon the foregoing, it will be appreciated that the disclosed methods may implement PA-GFP to enable or to facilitate the study of in vivo protein lifetimes in cell biology. In some embodiments, application of photoactivation processes may aid in systematic image segmentation for the study of cellular components; such image segmentation may also be employed for the study of cell migration in developmental biology, in chemotaxis, in diapedesis and immunology, and other fields. Additionally, PA-GFP may be employed in the study of protein proximity when used in conjunction with FRET techniques.

Aspects of the present invention have been illustrated and described in detail with reference to particular embodiments by way of example only, and not by way of limitation. It will be appreciated that various modifications and alterations may be made to the exemplary embodiments without departing from the scope and contemplation of the present disclosure. It is intended, therefore, that the invention be considered as limited only by the scope of the appended claims

What is claimed is:

1. A method of acquiring image data of an object; said method comprising:
   selectively inducing photoactivation of material at a site on the object;
   performing an optical axis integration scan;
   executing a time delay integration scan sequence; and
   selectively repeating said performing and said executing.

* * * * *